US00PP08616P

United States Patent [19]

Marciel et al.

[11] Patent Number: Plant 8,616

[45] Date of Patent: Mar. 1, 1994

[54] GRANDIFLORA ROSE PLANT NAMED DEVUNICAN

[75] Inventors: Stanley G. Marciel; Jeanne A. Marciel, both of Aptos, Calif.

[73] Assignee: DeVor Nurseries, Inc., Watsonville, Calif.

[21] Appl. No.: 974,117

[22] Filed: Nov. 10, 1992

[51] Int. Cl.[5] ..... A01H 5/00

[52] U.S. Cl. ..... Plt./15

[58] Field of Search ..... Plt. 15, 24

*Primary Examiner*—Howard J. Locker

*Attorney, Agent, or Firm*—Christie, Parker & Hale

[57] ABSTRACT

A new grandiflora rose plant producing yellow flowers.

1 Drawing Sheet

SUMMARY OF THE INVENTION

The present invention relates to a new and distinct variety of rose plant of the grandiflora rose class which was originated by my crossing as seed parent the variety known as 'Golden Fantasie' (U.S. Plant Pat. No. 3,272) and as pollen parent the variety known as 'Excitement' (U.S. Plant Pat. No. 4,412). The varietal denomination of this new rose is 'Devnunican'.

Among the novel characteristics possessed by this new variety which distinguish it from its parents and all other varieties of which I am aware are its attractive, deep intense golden yellow flowers borne on strong long stems having long vase life (10 to 12 days), particularly suited for growing in greenhouses.

Asexual reproduction by budding as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Golden Fantasie'.

*Pollen parent.*—'Excitement'.

Class: Grandiflora.

The following is a detailed description of specimens of the new variety, grown under glass in Watsonville, Calif. in September, with color terminology in accordance with The Royal Horticultural Society Colour Chart (RHSCC). The terminology used in color descriptions herein refers to plate numbers in the aforementioned color chart. Phenotypic expression may vary with light and cultural conditions.

FLOWER

Blooming habit: Continuous.

A. Bud:

(1) *Size.*—Small.

(2) *Form.*—Globular.

(3) *Color.*—As sepals divide, bud color is near 13A.

(4) *Sepals.*—Longer than bud; foliaceous. Color: Near 144A.

(5) *Peduncle.*—Length: About 8.5 to 9.5 cm. Aspect: Straight with small prickles. Strength: Erect. Color: Near 146B.

(6) *Bracts.*—1 to 2, near 147A, serrated, broadly elliptical, about 8 to 8.5 cm below calyx.

B. Bloom:

(1) *Size.*—Average size when fully expanded — about 10 to 11 cm.

(2) *Borne.*—Primarily singly, one to a stem.

(3) *Form.*—Imbricated, with petals rolling under at maturity.

(4) *Petalage.*—Number of petals under normal conditions — about 22 to 26; usually 5 to 7 petaloids.

(5) *Color.*—When ⅓ to ½ open, the top surface of the outer petals is near 17C with near 17A at the base. The undersurface of the outer petals is near 15C at the tip, near 13B at the center and near 15B at the base. The top surface of the inner petals is near 15B at the tip, near 14A at the center and near 17A at the base. The undersurface of the inner petals is near 16C at the tip, near 14C at the center and near 15A at the base. The base of the petals at the point of attachment is near 15A, and the general tonality from a distance is golden yellow. When fully open, the top surface of the outer petals is near 14B with near 11A at the base. The undersurface of the outer petals is near 10D at the tip, near 13C at the center and near 13B at the base. The top surface of the inner petals is near 13C at the tip, near 13B at the center and near 13A at the base. The undersurface of the inner petals is near 12C at the tip, near 13C at the center and near 13B at the base. The base of the petals at the point of attachment is near 13B, and the general tonality from a distance is yellow. As the bloom ages, the color lightens to a lighter shade of yellow. The petal top surface become near 13A; the petal undersurface becomes near 13B and the general tonality at a distance is yellow.

C. Petals:

(1) *Texture.*—Medium.

(2) *Appearance.*—Inside and outside smooth.

(3) *Form.*—Slightly lobed.

(4) *Arrangement.*—Regularly arranged, imbricated.

(5) *Fragrance.*—Slight musk.

(6) *Lasting quality.*—10 to 12 days as cut flower, petals drop cleanly.

REPRODUCTIVE ORGANS

A. Stamens:
- (1) *Arrangement.*—Introrse, near 22A.
- (2) *Anthers.*—Color — near 22A.
- (3) *Filaments (threads).*—Color — near 14A.
- (4) *Pollen.*—Color — near 22A.

B. Pistils:
- (1) *Styles.*—Bunched, medium length.
- (2) *Stigmas.*—Color — near 162A.

C. Characteristics of hips:
- (1) *Shape.*—Obovate; seeds do not protrude.
- (2) *Size.*—About 2.5 cm by 2.25 cm.
- (3) *Color at maturity.*—Near 26A.

PLANT

A. Form: Upright.

B. Growth: Very vigorous; height attained about 173 to 190 cm at first year.

C. Foliage: Compound 3 and 5 leaflets.
- (1) *Size.*—Medium.
- (2) *Quantity.*—Abundant.
- (3) *Color.*—New foliage, upper side — near 147A with a tinge of 184C around edges of both front and back; underside — near 189A. Old foliage, upper side — near 189A; underside — near 191A.
- (4) *Shape.*—Ovate.
- (5) *Texture.*—Leathery.
- (6) *Edge.*—Serrate.
- (7) *Serration.*—Denticulate.
- (8) *Leaf stem.*—Color — medium green.
- (9) *Stipules.*—Hairy, adnate.
- (10) *Petiole.*—Top — near 176B; bottom — near 146B with near 182B infused.
- (11) *Rachis.*—Small
- (12) *Auricle.*—Slender
- (13) *Resistance to disease.*—Under greenhouse conditions, no rust and black spot; good resistance to mildew.

D. Wood:
- (1) *New wood.*—Color — near 147B with tinges of near 183D. Bark — smooth.
- (2) *Old wood.*—Color — near 147B. Bark — smooth.

E. Flower stem: 85% between 38 and 66 cm.

F. Thorns:
- *Quantity (main stalk).*—Ordinary.
- *On laterals from stalk.*—Few.
- *Form.*—Thin, straight.
- *Length.*—Long.
- *Color.*—Near 184B at base, with 199A and 144B at tip.
- *Position.*—Irregular.
- *Prickles.*—Some.

F. Winter hardiness: Greenhouse variety; wintered well in California.

We claim:

1. A new and distinct variety of rose plant of the grandiflora rose class, substantially as shown and described.

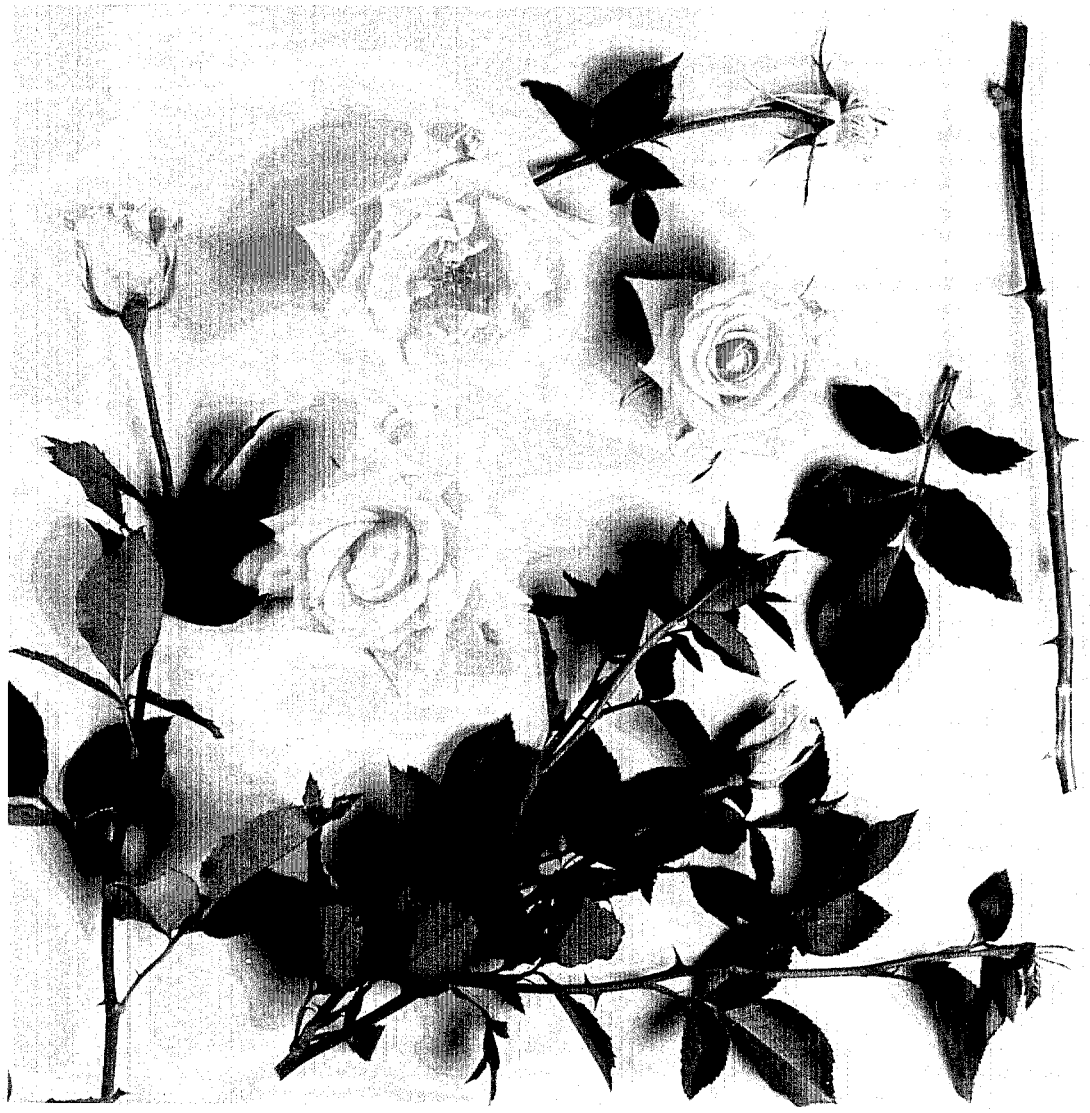

* * * * *